(12) United States Patent
Alevizopoulos (10) Patent No.: US 10,485,819 B2
(45) Date of Patent: Nov. 26, 2019

(54) IONIC AQUEOUS POLYSACCHARIDE COMPOSITIONS

(71) Applicant: Gerolymatos International S.A., Kryoneri (GR)

(72) Inventor: Konstantinos Alevizopoulos, Yverdon-les-Bains (CH)

(73) Assignee: Gerolymatos International S.A., Kryoneri (GR)

(*) Notice: Subject to any disclaimer, the term of this patent is extended or adjusted under 35 U.S.C. 154(b) by 100 days.

(21) Appl. No.: 15/100,187

(22) PCT Filed: Nov. 28, 2014

(86) PCT No.: PCT/EP2014/075983
§ 371 (c)(1),
(2) Date: May 27, 2016

(87) PCT Pub. No.: WO2015/082356
PCT Pub. Date: Jun. 11, 2015

(65) Prior Publication Data
US 2017/0000817 A1   Jan. 5, 2017

Related U.S. Application Data

(60) Provisional application No. 61/911,071, filed on Dec. 3, 2013.

(51) Int. Cl.
| | | |
|---|---|---|
| *A61K 36/03* | (2006.01) | |
| *A61K 31/737* | (2006.01) | |
| *A61K 36/04* | (2006.01) | |
| *A61K 36/53* | (2006.01) | |
| *A61K 45/06* | (2006.01) | |
| *A61K 31/164* | (2006.01) | |
| *A61K 31/197* | (2006.01) | |
| *A61K 9/00* | (2006.01) | |
| *A61K 9/08* | (2006.01) | |
| *A61K 35/747* | (2015.01) | |
| *A61K 35/748* | (2015.01) | |
| *A61K 47/02* | (2006.01) | |

(52) U.S. Cl.
CPC .......... *A61K 31/737* (2013.01); *A61K 9/0043* (2013.01); *A61K 9/08* (2013.01); *A61K 31/164* (2013.01); *A61K 31/197* (2013.01); *A61K 35/747* (2013.01); *A61K 35/748* (2013.01); *A61K 36/03* (2013.01); *A61K 36/04* (2013.01); *A61K 36/53* (2013.01); *A61K 45/06* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 6,451,352 B1* | 9/2002 | Yvin | A61K 35/08 424/600 |
| 7,541,052 B1 | 6/2009 | Cordray | |
| 2007/0135377 A1 | 6/2007 | Roman et al. | |
| 2007/0224216 A1* | 9/2007 | Teas | A61K 35/748 424/195.17 |
| 2010/0209461 A1* | 8/2010 | Jensen | A61K 35/748 424/400 |
| 2013/0065851 A1* | 3/2013 | Fitton | A61K 31/737 514/56 |
| 2014/0213545 A1* | 7/2014 | Remmereit | A61K 31/05 514/54 |
| 2015/0359828 A1 | 12/2015 | Dragar et al. | |

FOREIGN PATENT DOCUMENTS

| | | | |
|---|---|---|---|
| CN | 1123146 A | | 5/1996 |
| CN | 1526328 A | | 9/2004 |
| CN | 1660382 A | | 8/2005 |
| CN | 102028945 A | | 4/2011 |
| DE | 20 2009 014631 | * | 1/2010 |
| EP | 1466969 A1 | | 10/2004 |
| JP | 2000 229832 | * | 8/2000 |
| JP | 2000229832 A | | 8/2000 |
| JP | 2001 181303 | * | 7/2001 |
| JP | 2001181303 A | | 7/2001 |
| JP | 2007061058 A | | 3/2007 |

(Continued)

OTHER PUBLICATIONS

Kehri W. et al. Dexpanthenol Nasal Spray as an Effective Therapeutic Principle for Treatment of Rhinitis Sicca Anterior. Laryngorhiniootologie 77(9)506-12, Sep. 1998. (Year: 1998).*
Alevizopoulos, K. Hypertonic Seawater Solutions Comprising Algae Extracts . . . Allergy: European J of Allergy and Clinical Immunology 72(Suppl 103)194, Abstract No. 0574 Aug. 2017. (Year: 2017).*
Hayashi, T. Studies on Evaluation of Natural Products for Antiviral Effects and Their Applications. Yakugaku Zasshi 128(1)61-79 2008. (Year: 2008).*
Basch E et al., Thyme (*Thymus vulgaris* L.), Thymol, Journal of Herbal Pharmacotherapy, Haworth Herbal Press, Binghamton, US, vol. 4, No. 1, Jan. 2004 , pp. 49-67.

(Continued)

*Primary Examiner* — Ralph J Gitomer
(74) *Attorney, Agent, or Firm* — Dentons US LLP (57) ABSTRACT

Disclosed herein are ionic aqueous compositions useful as nasal passage washes to aid in the resorption of edema of the respiratory mucosa, e.g., the nasal mucosa, for the treatment of respiratory tract and/or respiratory mucosal-related conditions, including, e.g., chronic rhinosinusitis, sinusitis, allergic rhinitis and nasal polyps. The composition includes an ionic aqueous solution and algae-derived constituents, such as branched, sulfated polysaccharides having an average molecular weight greater than 4 kDa and comprising L-fucose and sulfate ester groups or extracts from brown algae. Also disclosed are methods and pharmaceutical compositions for treating respiratory tract and/or respiratory mucosal-related conditions, including, e.g., chronic rhinosinusitis.

15 Claims, 2 Drawing Sheets

(56) References Cited

FOREIGN PATENT DOCUMENTS

| JP | 2008063241 A | 3/2008 |
|---|---|---|
| WO | WO2010/000437 | 1/2010 |
| WO | WO2011/100805 | 8/2011 |

OTHER PUBLICATIONS

Cingi et al., The effects of spirulina on allergic rhinitis, European Archives of Oto-Rhino-Laryngology; Mar. 2008, vol. 265, No. 10, pp. 1219-1223.
CN1123146 published May 29, 1996, Abstract Only downloaded from espacenet May 23, 2016 (1 page).
CN1526328 published Sep. 8, 2004, Abstract Only downloaded from espacenet May 23, 2016 (1 page).
CN1660382 published Aug. 31, 2005, Abstract Only downloaded from espacenet May 23, 2016 (1 page).
CN102028945 published Apr. 27, 2011, Abstract Only downloaded from espacenet May 23, 2016 (1 page).
Hayashi, Studies on evaluation of natural products for antiviral effects and their applications, Pharmaceutical Society of Japan, 2008, vol. 128, No. 1, pp. 61-79.
International Search Report and Written Opinion dated Jan. 30, 2015 in corresponding International Application No. PCT/EP14/75983 filed Jan. 28, 2014 (15 pages).
JP2000229832 published Aug. 22, 2000, Abstract Only downloaded from espacenet May 23, 2016 (1 page).
JP2001181303 published Jul. 3, 2001, Abstract Only downloaded from espacenet May 23, 2016 (1 page).
JP2007061058 published Mar. 15, 2007, Abstract Only downloaded from espacenet May 23, 2016 (1 page).
JP2008063241 published Mar. 21, 2008, Abstract Only downloaded from espacenet May 23, 2016 (1 page).
Roehm et al., The Role of Alternative Medicine in Rhinology, Facial Plastic Surgery Clinics of North America, vol. 20, No. 1, Feb. 2012, pp. 73-81.
EP Office Action dated Apr. 24, 2018 in related Application No. 14805880.3 filed Nov. 28, 2014 (4 pages).
Ale et al., Important Determinants for Fucoidan Bioactivity: A Critical Review of Structure-Function Relations and Extraction Methods for Fucose-Containing Sulfated Polysaccharides from Brown Seaweeds, Marine Drugs, 2011, vol. 9,10, pp. 2106-2130.
Anastase-Ravion et al., Heparin-like polymers modulate proinflammatory cytokine production by lipopolysaccharide-stimulated human mononcytes, J Biomed Mater Res, 2002, 60(3):375-383.

* cited by examiner

IONIC AQUEOUS POLYSACCHARIDE COMPOSITIONS

The present application claims the benefit of priority to PCT International Application No. PCT/EP2014/075983 filed 28 Nov. 2014, which claims the benefit of U.S. Provisional Application Ser. No. 61/911,071 filed 3 Dec. 2013, each of which is incorporated herein by reference in its entirety.

BACKGROUND OF THE INVENTION

Sinonasal complaints affect at least 15% of the population in the United States of America with predictable patient morbidity and financial impact. Importantly, any modality that can alleviate sinonasal complaints warrants serious attention. Among various treatments utilized in this setting, nasal irrigation is considered a simple, inexpensive and beneficial approach that can be applied in concert with existing prescribed medications such as steroids, anti-histamines, vasoconstrictors and other drugs or as part of treatment modalities that help alleviate sinonasal symptoms such as nasal obstruction, rhinorrhea and others.

The principal functions of the nasal passages are the regulation of the inspiratory air flow, the heating and humidification of inspired air and the elimination of foreign elements (dust, microbial germs). The ciliate epithelium, which covers the nasal mucosa, plays a vital role in its defense from infections. The vibratile cilia of this epithelium are immersed in protective mucus, which surrounds them, and their purpose is to push this mucous, together with any external impurities, posteriorly, i.e., towards the pharynx, by their motions.

Seawater-based compositions currently available for rinsing the nasal passages are generally prepared so that they are isotonic with the nasal mucosa. These compositions usually consist of a mixture of seawater and deionized water, such that the per volume fraction of seawater in this mixture is approximately one-third. Alternatively, the compositions consist of increased per volume seawater fractions resulting in hypertonic solutions. These are believed to have better cleansing properties due to the generation of osmotic gradients that allow for more efficacious mucus removal in comparison to isotonic solutions.

However, and despite their widespread use for cleansing and symptomatic relief of sinonasal conditions, these solutions, typically packaged in the form of aerosol sprays, provide little or no therapeutic benefits against the causes of the disease. Furthermore, and in cases where the seawater compositions are complemented with additional ingredients thought to improve their action, such as exogenous salts, anti-septic anti-bacterial agents, amino acids, essential oils and other agents, they suffer from limited industrial applicability due to various factors. These include poor water solubility of added ingredients, label restrictions and/or burning sensations (e.g. in the case of essential oils; these cannot be used in children according to WHO guidelines), limited compatibility of added ingredients to the high salt content present in (hypertonic) solutions, increased cost or other limitations.

For this reason, better seawater and/or saline solutions with improved efficacy and negligible side effects are sought.

SUMMARY OF THE INVENTION

As described below, the present invention features compositions for nasal administration and methods of treating respiratory tract and/or respiratory mucosal-related conditions.

In one aspect, a composition includes an ionic aqueous solution and a sulfated polysaccharide having an average molecular weight greater than 4 kDa and comprising L-fucose and sulfate ester groups. In one embodiment, the composition is formulated for nasal administration.

In one embodiment, the sulfated polysaccharide is derived from an extract isolated from brown algae. In another embodiment, the brown algae is *Undaria pinnafitida*. In another embodiment, the sulfated polysaccharide is fucoidan. In yet another embodiment, the sulfated polysaccharide is in a range of about 0.1 to about 10% weight content of the composition.

In another embodiment, the composition further includes an extract of a blue/green algae, e.g., such as an extract isolated from *Spirulina platensis*. In one embodiment, the blue/green algae extract is in a range of about 0.1 to about 10% weight content of the composition.

In yet another embodiment, the composition further includes a sulfated, galactose-based polysaccharide having an average molecular weight greater than about 15 kDa. In one embodiment, the galactose-based polysaccharide is a carrageenan. In yet another embodiment, the carrageenan is selected from the group consisting of iota-carrageenan, kappa-carrageenan, and lambda-carrageenan. In a particular embodiment, the carrageenan is iota-carrageenan.

In another embodiment, the galactose-based polysaccharide is derived from an extract isolated from red algae. In yet another embodiment, the galactose-based polysaccharide is an iota-carrageenan derived from the red algae extract isolated from *Gigartina stellata* or *Chondrus chrispus*. In still another embodiment, the galactose-based polysaccharide is a kappa-carrageenan derived from the red algae extract isolated from *Kappaphycus cottonii*. In one embodiment, the red algae is selected from *Gigartina stellata, Chondrus chrispus, Kappaphycus cottonii*. In another embodiment, the galactose-based polysaccharide is in a range of about 0.1 to about 10% weight content of the composition. In yet another embodiment, the composition includes both a sulfated, galactose-based polysaccharide having an average molecular weight greater than about 15 kDa and an extract of a blue/green algae.

In yet another embodiment, the ionic aqueous solution includes seawater. In a particular embodiment, the seawater includes undiluted seawater. In a particular embodiment, the seawater includes (i.e. is diluted with) at least one of purified, distilled, deionized, and filtered water. In another embodiment, the ionic aqueous solution includes saline. In still yet another embodiment, the ionic aqueous solution includes about 10 to about 99.9% weight content of the composition.

In another embodiment, the composition has an osmolarity value ranging from about 250-350 mOsm/L for isotonic, greater than about 350 mOsm/L for hypertonic and less than about 250 mOsm/L for hypotonic. In yet another embodiment, the composition further includes at least one of exogenous salts, anti-microbial agents, amino acids, and essential oils.

In another aspect, a use of the composition is provided for the manufacture of a medicament or product for alleviating a respiratory tract and/or respiratory mucosal-related condition. In one embodiment, the composition is formulated for nasal administration. In another embodiment, the use is for a respiratory tract and/or respiratory mucosal-related condition selected from the group consisting of acute and chronic rhinosinusitis, sinusitis, allergic and non-allergic rhinitis, asthma, cystic fibrosis, chronic obstructive pulmonary disease (COPD), and other diseases of the respiratory tract.

In yet another aspect, a composition for nasal administration comprising an ionic aqueous solution and an extract from brown algae is provided. In one embodiment, the brown algae extract is in a range of about 0.1 to about 10% weight content of the composition. In another embodiment, the composition also includes an extract from a blue/green algae. In a particular embodiment, the blue/green algae extract is in a range of about 0.1 to about 10% weight content of the composition. In yet another embodiment, the composition further includes an extract from a red algae. In one particular embodiment, the red algae extract is in a range of about 0.1 to about 10% weight content of the composition. In another embodiment, the ionic aqueous solution comprises at least one of seawater or saline solution. In still another embodiment, the composition further includes at least one of exogenous salts, anti-microbial agents, amino acids, and essential oils. In yet another embodiment, the composition further includes at least one of a corticosteroid, other steroidal compound, anti-histamine, decongestant, bronchodilator, β2-adrenergic agonist, and antibiotic. In another embodiment, the composition further includes at least one plant extract. In another embodiment, the composition further includes at least one hydrating agent.

In still another aspect, pharmaceutical compositions of the herein described compositions are provided.

In another aspect, a pharmaceutical composition for treatment of a respiratory tract and/or respiratory mucosal-related condition includes an ionic aqueous solution, an extract from brown algae and a pharmaceutically acceptable carrier or adjuvant. In one embodiment, the ionic aqueous solution comprises at least one of seawater or saline solution. In another embodiment, the respiratory tract and/or respiratory mucosal-related condition is selected from the group consisting of acute and chronic rhinosinusitis, sinusitis, allergic and non-allergic rhinitis, asthma, cystic fibrosis, chronic obstructive pulmonary disease (COPD), and other diseases of the respiratory tract. In yet another embodiment, the pharmaceutical composition further includes an extract from a blue/green algae. In still yet another embodiment, the pharmaceutical composition further includes at least one of exogenous salts, anti-microbial agents, amino acids, and essential oils. In yet another embodiment, the composition further includes at least one of a corticosteroid, other steroidal compound, anti-histamine, decongestant, bronchodilator, β2-adrenergic agonist, and antibiotic.

In yet another aspect, a method is provided for treating a respiratory tract and/or respiratory mucosal-related condition in a subject in need thereof by aerosolizing the pharmaceutical composition described herein in a nasal passageway of the subject. In one embodiment, the subject is a human subject. In another embodiment, the respiratory tract and/or respiratory mucosal-related condition is selected from the group consisting of acute and chronic rhinosinusitis, sinusitis, allergic and non-allergic rhinitis, asthma, cystic fibrosis, chronic obstructive pulmonary disease (COPD), and other diseases of the respiratory tract. In a particular embodiment, the respiratory tract and/or respiratory mucosal-related condition is rhinosinusitis.

In still yet another aspect, a packaged device is provided that includes the pharmaceutical composition described herein optionally together with instructions for use. In one embodiment, the device is selected from the group consisting of aerosol dispenser, pneumatically pressurized device, multi-dose metered dose spray pump, inhaler, pump sprayer, and nebulizer.

Definitions

Unless defined otherwise, all technical and scientific terms used herein have the meaning commonly understood by a person skilled in the art to which this invention performs. As used herein, the following terms have the meanings ascribed to them below, unless specified otherwise.

By "algae extract" is meant any fraction, or isolated or purified molecule from an algae cell. The extract can include proteins or glycoproteins or nucleic acids. Examples of algae extract include brown algae extract (e.g., *Undaria pinnafitida*), blue-green algae extract (e.g., *Spirulina platensis*), and red algae extract (e.g., *Gigartina stellata, Chondrus chrispus*, and *Kappaphycus cottonii*).

By "fucose-based polysaccharide" includes fucan sulfate, fucose-rich sulfated polysaccharides, a rhamnose-containing sulfated polysaccharide, a galactofucan and the like. The term "fucoidan" may also be used to describe the fucose-based polysaccharides from brown seaweeds, as well as physically, chemically and/or enzymatically derivatized forms thereof.

The term "galactose-based polysaccharide" includes D-galactoses bonded by alpha (1-3) and beta (1-4) bonds, carrageenans (iota-, kappa- and lambda-carrageenan that differ slightly in their structure and degree of sulfation), linear or branched sulfated galactose-based polysaccharides and the like. The term "carrageenan" may also be used to describe the galactose-based polysaccharides extracted from red edible seaweed, as well as physically, chemically and/or enzymatically derivatized forms thereof.

By "respiratory tract and/or respiratory mucosal-related conditions," are meant any conditions or disorders with abnormal mucus production, secretion or clearance or inflammation (bacterial, viral, allergic or autoimmune) of the nasal, bronchial and pulmonary mucosa. Examples of diseases include acute rhinosinusitis, recurrent acute rhinosinusitis, subacute rhinosinusitis, chronic rhinosinusitis, acute exacerbation of chronic rhinosinusitis, sinusitis, allergic and non-allergic rhinitis, asthma, cystic fibrosis, chronic obstructive pulmonary disease (COPD), and other diseases of the upper and lower respiratory tract.

By "agent" is meant any small molecule compound or mixes thereof synthesized chemically or derived from natural sources (e.g. herbal extracts), antibody, nucleic acid molecule, or polypeptide, or fragments thereof.

By "ameliorate" is meant decrease, suppress, attenuate, diminish, arrest, or stabilize the development or progression of a disease.

In this disclosure, "comprises," "comprising," "containing" and "having" and the like have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "effective amount" is meant the amount of a composition of the invention required to ameliorate the symptoms of rhinosinusitis of an untreated patient. The effective amount of active compound(s) used to practice the present invention for therapeutic treatment of rhinosinusitis varies depending upon the manner of administration, the age, body weight, and general health of the subject. Ultimately, the attending physician or veterinarian will decide the appropriate amount and dosage regimen. Such amount is referred to as an "effective" amount.

A "fraction" of an organism, such as a species of algae, is any isolated or purified molecule or complex of molecules.

A fraction can be obtained by any method known in the art by which molecules are isolated or purified from a cell, such as by extraction or ultracentrifugation. In particular examples, a fraction of algae is produced by extraction of the algae cell followed by further isolation of molecules of a particular molecular weight range or size. In particular examples, a fraction is in liquid form. In other examples, a fraction is in a solid form, such as a dried form. In still other examples, a fraction can be formulated as an aerosolized particulate.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" polysaccharide is sufficiently free of other materials such that any impurities do not materially affect the biological properties of the polysaccharide or cause other adverse consequences. That is, a polysaccharide of this invention is purified if it is substantially free of cellular or other materials when isolated or chemically synthesized. Purity and homogeneity are typically determined using analytical chemistry techniques, for example, electrophoresis or thin layer chromatography. The term "purified" can denote that a material that is enriched in polysaccharides by removing proteins and/or DNA.

As used herein, "obtaining" as in "obtaining an agent" includes synthesizing, purchasing, or otherwise acquiring the agent.

As used herein, the terms "prevent," "preventing," "prevention," "prophylactic treatment" and the like refer to reducing the probability of developing respiratory tract and/or respiratory mucosa-related conditions, e.g., rhinosinusitis or inflammatory condition, in a subject, who does not have, but is at risk of or susceptible to developing such conditions.

By "reduces" is meant a negative alteration of at least 10%, 25%, 50%, 75%, or 100%.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein "% weight content" means % w/w. All percentage values mentioned herein are % w/w unless indicated otherwise.

As used herein, a "substantially similar composition" in relation to a reference formulation means a formulation having the same components in the same concentration as in the reference, or wherein the concentration of any of the components differs relative to the reference in an immaterial way.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

This invention provides seawater-based compositions. Compositions with ingredients that are widely abundant, easily isolated by naturally growing organisms, intrinsically compatible with seawater and/or saline solutions of all types of osmolarities and generally recognized as safe, are particularly appealing for the development of new solutions with improved efficacy and negligible side effects. The compositions described herein are believed to satisfy all these conditions.

The compositions can be useful as nasal passage washes to aid in the resorption of edema of the nasal mucosa, and/or for the treatment of respiratory tract and/or respiratory mucosal-related conditions, such as chronic rhinosinusitis, sinusitis, allergic rhinitis, nasal polyps, and other nasal conditions and/or inflammatory conditions of nasal, bronchial and respiratory mucosa. The composition includes an ionic aqueous solution and algae-derived constituents, such as sulfated polysaccharides having an average molecular weight greater than 4 kDa and comprising L-fucose and sulfate ester groups. The sulfated polysaccharides may be linear or branched.

The composition can be applied in the form of a nasal spray (or alternatively in an aerosolized/nebulized form for inhalation) to patients with various inflammatory and other conditions affecting the nasal, bronchial and pulmonary mucosa caused by various agents (e.g. substances of bacterial origin, viruses, bacteria, irritants, allergens etc). Some nonlimiting examples of inflammatory conditions include: acute and chronic rhinosinusitis, allergic and non-allergic rhinitis, asthma, cystic fibrosis, chronic obstructive pulmonary disease (COPD), other diseases of the respiratory tract, and others.

Compositions

Described herein are compositions, such as seawater-based compositions, intended for administration to and through the respiratory tract, e.g., via nasal administration. The compositions can include a mixture of previously filtered, purified and sterilized seawater and an algae-based constituent. In one aspect, the invention provides a composition with an ionic aqueous solution and an algal extract, such as brown algae. Compositions of seawater including ionic aqueous solutions, such as saline or seawater solutions, and algae-derived constituents are described further below.

Ionic Aqueous Solutions

Compositions of the invention can include an ionic aqueous solution that is filtered and/or sterilized. Ionic aqueous solutions can be classified into two different categories: saline solutions and seawater solutions.

Seawater sterilization has been previously described. EP 0909184 also describes relative percentages of magnesium, calcium, potassium, zinc and copper presented in seawater collected in Cancale Bay. Additional sites in the same area (Saint Malo) can also be used as the sources of seawater, see FR2915389. The seawater collected can be diluted to different extents with purified/filtered/deionized water or used for selective electrodialysis to alter the different ionic concentrations, see also WO/2012/110665.

Saline solutions can refer to aqueous solutions comprising various concentrations of sodium chloride (NaCl) including: (1) normal or isotonic saline solutions: solutions containing from about 0.9% w/v of NaCl and an osmolarity of about 300 mOsm/L; (2) hypotonic saline, solutions containing NaCl of less than about 0.9% NaCl and less than about 300 mOsm/L, see for example U.S. Pat. No. 8,337,906; and (3) hypertonic saline solutions containing NaCl of greater than about 0.9% NaCl and greater than about 300 mOsm/L. For example, solutions of 3% and 5% NaCl would have osmolarities of about 1000 mOsm/L and about 1700 mOsm/L, respectively.

The saline solutions can include additional salts, such as the non-limiting examples of, Dead Sea salts and antioxidants, as exemplified by U.S. Pat. No. 7,541,052, see also U.S. Pat. No. 6,528,081. Optional additional ingredients can could include zinc, as exemplified by U.S. Pat. No. 5,622,724, copper, manganese, magnesium and other metal ions, anti-microbial agents, essential oils, etc, see also WO/2003/015746 and WO/2012/110665. These solutions may have the pH adjusted, i.e. to physiological levels (pH 7-8) using a variety of buffers. Saline solutions may also include hypertonic (U.S. Pat. No. 7,541,052) or hypotonic saline solutions.

Seawater solutions can refer to three types of solutions: (1) undiluted seawater; (2) diluted seawater; and (3) ion content/osmolarity altered seawater.

Undiluted seawater contains a multitude of ingredients, see Table 1 below; these include various salts, minerals and trace elements. It is noted that the ionic content/strength of seawater is measured in 2 ways: either as sodium chloride equivalents or via direct measurements of osmolarity (e.g., about 1000 mOsm/L).

In the former case, NaCl equivalents are calculated using methods, such as the Volhard method. In this case, the method precipitates all chlorides in seawater ("halides" e.g. Na, K, Ca, Mg salts with Cl) and converts them into a percentage of NaCl. Accordingly, undiluted seawater has about 3.1-3.8% w/v NaCl (depending on the origin of seawater).

Regarding the osmolarity measurements of pure seawater, it is noted that the contribution of different ions (in mOsm) in the about 1000 mOsm/L value are: Na: 459, K: 10, Ca: 10, Mg: 53, Cl: 538. Seawater used in this case is typically filtered and/or sterilized to remove/eliminate microorganisms before use.

Seawater can be diluted to different degrees with purified/distilled/deionized/filtered water. Depending on the diluting factor, solutions can be rendered hypotonic, isotonic or increasingly less hypertonic in comparison to undiluted seawater. For example, a 7:3 dilution is described in EP 0908184, which is incorporated by reference in its entirety. This results in a hypertonic solution comprising about 2.3-2.5% NaCl (equivalents). Additional dilutions can also be done to give solutions with about 0.9, 2, 2.6 or 3% NaCl, see for example U.S. Pat. No. 4,581,226, (also Tables 1 and 3). It is obvious that the osmolarity of seawater is also changing according to dilution.

Ion content/osmolarity of seawater can also be artificially altered by chemicals means, e.g. electrodialysis to specifically reduce the content of ions to the desired extent (e.g., to about 0.9% NaCl rendering the solution iso-osmotic) or to about 2.2% (hyperosmotic). Typical solutions of this kind are described in EP 1091747 or US2010/0151044 (iso-osmotic) or WO/2008/037938 and WO/2012/110665 (hyper-osmotic).

The difference between diluted and electrodialyzed seawater solutions is that apart from the differential percentage of NaCl, seawater ingredients are diluted in the former case whereas in the latter case they remain as they are in pure seawater. The relevance of this information is explained below, see also Tables 2 and 3 below for a direct comparison between ion contents in both methods. It is noted that as pure seawater has various %s of the different ingredients to start with, so there is some variability in the preparation of solutions in each case.

TABLE 1

Composition of seawater from "Handbook of Chemistry and Physics" 63$^{rd}$ edition 1982-1983, CRC Press, see also Table A of US2010/0151044.

| Element | Quantity (ppm) | Element | Quantity (ppm) |
|---|---|---|---|
| Cl | 18,980 | Pb | 0.004-0.005 |
| Na | 10,561 | Se | 0.004 |
| Mg | 1,272 | Sn | 0.003 |
| S | 884 | Cs | 0.002 (approximately) |
| Ca | 400 | U | 0.00015-0.0016 |
| K | 380 | Mo | 0.0003-0.002 |
| Br | 65 | Ga | 0.0005 |
| C (inorganic) | 28 | Ni | 0.0001-0.0005 |
| Sr | 13 | Th | <0.0005 |
| (SiO2) | 0.01-7.0 | Ce | 0.0004 |
| B | 4.6 | V | 0.0003 |
| C (organic) | 1.2-3.0 | La | 0.0003 |
| Al | 0.16-1.9 | Y | 0.0003 |
| F | 1.4 | Hg | 0.00003 |
| N (nitrate) | 0.001-0.7 | Ag | 0.00015-0.0003 |
| N (organic nitrogen) | 0.03-0.2 | Bi | 0.0002 |
| Rb | 0.2 | Co | 0.0001 |
| Li | 0.1 | Sc | 0.00004 |

TABLE 1-continued

Composition of seawater from "Handbook of Chemistry and Physics" 63rd edition 1982-1983, CRC Press, see also Table A of US2010/0151044.

| Element | Quantity (ppm) | Element | Quantity (ppm) |
|---|---|---|---|
| P (phosphate) | >0.001-0.10 | Au | 0.000004-0.000008 |
| Ba | 0.05 | Fe (in true solution) | <10-9 |
| I | 0.05 | Ra | 2.10-11 = 3.10--10 |
| N (nitrite) | 0.0001-0.05 | Ge | Present |
| N (ammoniac) | >0.005-0.05 | Ti | Present |
| As (arsenic) | 0.003-0.024 | W | Present |
| Fe | 0.002-0.02 | Cd | Present in marine organisms |
| P (organic phosphorus) | 0.016 | Cr | Present in marine organisms |
| Zn | 0.005-0.014 | Tl | Present in marine organisms |
| Cu | 0.001-0.09 | Sb | Present in marine organisms |
| Mn | 0.001-0.01 | Zr | Present in marine organisms |
|  |  | Pt | Present in marine organisms |

TABLE 2

Ion content/osmolarity altered by seawater dilution to specifically reduce the content of ions to the desired extent

|  |  | Pure Seawater* | Isotonic | Hypertonic | | |
|---|---|---|---|---|---|---|
|  |  | (mg/L)** | | | | |
| % Sodium Chloride | NaCl*** | 3.50% | 0.90% | 2.00% | 2.30% | 2.60% | 3.00% |
| Sodium | Na+ | 10,500 | 2,700 | 6,000 | 6,900 | 7,800 | 9,000 |
| Chloride | Cl− | 19,000 | 4,886 | 10,857 | 12,486 | 14,114 | 16,286 |
| Potassium | K+ | 390 | 100 | 223 | 256 | 290 | 334 |
| Calcium | Ca++ | 410 | 105 | 234 | 269 | 305 | 351 |
| Magnesium | Mg++ | 1,350 | 347 | 771 | 887 | 1,003 | 1,157 |
| Sulfate | SO4−− | 2,700 | 694 | 1,543 | 1,774 | 2,006 | 2,314 |

*pure seawater values are taken from Langmuir (1997): Aqueous environmental geochemistry: Upper Saddle River, Prentice Hall, Inc., 600p
**depicted values will vary 5-10% depending on origin of seawater
***calculated as NaCl equivalents (Volhard method)

TABLE 3

Ion content/osmolarity altered by electrodialysis to specifically reduce the content of ions to the desired extent

|  |  | Pure Seawater | Iso-Osmotic | Hyper-Osmotic |
|---|---|---|---|---|
|  |  |  | (mg/L) |  |
| % Sodium Chloride | NaCl | 3.50% | 0.90% | 2.20% |
| Sodium | Na+ | 10,500 | 2100-2600 | 5500-7500 |
| Chloride | Cl− | 19,000 | 5400-6300 | 10000-13000 |
| Potassium | K+ | 390 | 44-62 | 100-250 |
| Calcium | Ca++ | 410 | 280-390 | 300-450 |
| Magnesium | Mg++ | 1,350 | 1100-1500 | 1100-1500 |
| Sulfate | SO4−− | 2,700 | 2,700 | 2,700 |

Algae Extracts

Compositions of the invention can also include algae extracts, such as sulfated polysaccharides obtained from algae extracts. Algae extracts can be obtained from three different algae: (1) brown algae; (2) blue and green algae; (3) and red algae.

Brown Algae Extracts

Also provided are compositions that include extracts from brown algae. Brown algae extracts and some marine invertebrates (such as sea urchins and sea cucumbers) are rich in sulfated polysaccharides. Sulfated polysaccharides obtained from brown algae extracts can have an average molecular weight greater than about 4 kDa. The sulfated polysaccharides can be linear or branched. The sulfated polysaccharides include fucose-based polysaccharides with L-fucose and sulfate ester groups, such as fucoidan. Fucoidans include those derived from brown algae, such as *Undaria pinnafitida*, or synthetic fucoidan polysaccharides, such as a high molecular weight fucoidan (HMWF) fraction having an average molecular weight ranging from about 1 to 2 MDa (e.g. Kraeber, Germany) and a low molecular weight fucoidan (LMWF) fraction having an average molecular weight of about 8.2 kDa, are useful.

Particular brown algae include species of *Ascoseira, Cutleria, Microzonia, Zanardinia, Arthrocladia, Desmarestia, Himantothallus, Phaeurusm, Dictyopteris, Dictyota, Dilophus, Distromium, Glossophora, Homoeostrichus, Lobophora, Lobospira, Newhousia, Pachydictyon, Padina, Spatoglossum, Stypopodium, Taonia, Zonaria, Scoresbyella, Choristocarpus, Discosporangium, Acinetospora, Feldmannia, Geminocarpus, Hincksia, Pogotrichum, Pylaiella, Adenocystis, Caepidium, Utriculidium, Acrothrix, Ascoseirophila, Asperococcus, Austrofilum, Chordaria, Cladosiphon, Corycus, Delamarea, Dictyosiphon, Elachista, Eudesme, Giraudia, Gononema, Halothrix, Haplogia, Hecatonema, Heterosaundersella, Hummia, Isthmoplea, Laminariocolax, Laminarionema, Leathesia, Leptonematella, Litosiphon, Microspongium, Mikrosyphar, Myelophycus, Myriogloea, Myrionema, Myriotrichia, Papenfussiella, Petrospongium, Pleurocladia, Polytretus, Proselachista, Protectocarpus, Punctaria, Sauvageaugloia, Soranthera, Sorocarpus, Spermatochnus, Sphaerotrichia, Stictyosiphon, Streblonema, Striaria, Stschapovia, Tinocladia, Chordariopsis, Asterocladon, Ectocarpus, Kuckuckia, Mesospora, Asterotrichia, Bachelotia, Bifurcariopsis, Durvillaea, Ascophyllum, Fucus, Hesperophycus, Pelvetia, Pelvetiopsis, Silvetia, Xiphosphora, Himanthalia, Hormosira, Notheia, Anthophycus, Axillariella, Bifurcaria, Bifurcariopsis, Carpoglossum, Caulocystis, Coccophora, Cystophora, Cystoseira, Halidrys, Hizikia, Hormophysa, Myagropsis, Myogropsis, Myriodesma, Sargassum, Turbinaria, Cystophaera, Marginariella, Phyllospora, Seirococcus, Ishige, Akkesiphy-* cus, *Alaria, Aureophycus, Druehlia, Eualaria, Hirome, Lessoniopsis, Pleurophycus, Pterygophora, Undaria, Undariella, Undariopsis, Chorda, Agarum, Costaria, Dictyoneurum, Thalassiophyllum, Arthrothamnus, Costularia, Cymathere, Feditia, Gigantea, Laminaria, Macrocystis, Nereocystis, Pelagophycus, Pelagophycus, Macrocystis, Phycocastanum, Phyllariella, Polyschidea, Postelsia, Pseudolessonia, Saccharina, Streptophyllopsis, Eckonia, Eckloniopsis, Egregia, Eisenia, Lessonia, Pseudochorda, Nemoderma, Onslowia, Verosphacella, Neoralfsia, Basispora, Hapalospongidion, Jonssonia, Lithoderma, Myrionemopsis, Petroderma, Porterinema, Pseudolithoderma, Ralfsia, Chnoospora, Colpomenia, Hydroclathrus, Petalonia, Rosenvingea, Scytosiphon, Bodanella, Coelocladia, Heribaudiella, Phaeostroma, Asteronema, Scytothamnus, Stereocladon, Splachnidium, Cladostephus, Sphacelaria, Sphacella, Alethocladus, Halopteris, Stypocaulon, Austronereia, Bellotia, Carpomitra, Encyothalia, Nereia, Perisporochnus, Perithalia, Sporochnema, Sporochnus, Tomaculopsis, Syringoderma, Halosiphon, Masonophycus, Phyllariopsis, Saccorhiza, Stschapovia, Haplospora, Phaeosiphoniella, Tilopteris, Neolepioneuma, Analipus* and *Phaeostrophion.*

Other sources include some green seaweeds and echinoderms such as sea urchins and sea cucumbers. Examples of green seaweed include *Ulva* sp, *Enteromorpha* sp, *Codium* sp, *Caulerpa* sp and *Halimala* sp.

The sulfated polysaccharides that include fucose-based polysaccharides, can include extracts derived from *Fucus vesiculosus* and contain mostly fucose, sulfate, ash, and traces of aminoglucose. Sulfated polysaccharides from brown algae *F. evanescens* C. Ag, *F. distichus* and *F. serratus* L. include mostly fucose, sulfate and acetate. Fucoidans include F-fucoidan, mainly composed of sulfated esters of fucose, and U-fucoidan, composed of about 20% of glucuronic acid. Some sulfated polysaccharides include alternating 3- and 4-linked α-L-fucopyranose 2-sulfate residues and others can include disaccharide repeating units. In addition to linear polysaccharides, highly branched structures are included in extract derived from *E. kurome* or *Chorda filum.*

The sulfated polysaccharides for use in the method and compositions described herein may include an extract from the whole plant or any part of the plant, such as the leaves, stem, spores, or a combination thereof. The starting material may be fresh, frozen or dried material. After filtration or dialysis, the extract may be used as a liquid or dried. Typically, such an extract includes from at least about 1% w/v fucose-based polysaccharide to about 100% w/v.

The sulfated polysaccharides are generally from about 4 kDa to about 5 MDa including about 5, 10, 15, 20, 30, 50, 70, 90, 100, 300, 500, 700, 900, 1000, 2000, 3000, 4000 and 5000 kDa or an average molecular weight in between these particular sizes.

The sulfated polysaccharides also include fucoidans described in patent application WO/2011/100805, see for example relevant information that can be used on MW (greater than about 4 kDa, preparations comprising various fucoidan contents e.g. about 10-95% or more), species that can be used for isolation, specifications of fucoidans used etc. Note that fucoidans used in the Examples are derived from *Undaria pinnatifida* (aqueous) extracts and comprise greater than about 85% of fucoidans.

In one embodiment, compositions include about 0.1% to about 10% sulfated polysaccharide or fucoidan weight content of the composition. The range of sulfated polysaccharide or fucoidan in the composition can be from about 0.1% to about 20%, about 0.1% to about 10%, about 0.1% to about 5%, and about 0.1% to about 1% weight content of the composition. In other embodiments, the composition includes at least about 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, or more % sulfated polysaccharide or fucoidan weight content.

Blue-Green Algae Extracts

The compositions of the invention may also include extracts from blue-green algae. Blue-green algae extracts are rich in protein, vitamins, minerals, and carotenoids, antioxidants that can help protect cells from damage. Extracts contain nutrients, including B complex vitamins, beta-carotene, vitamin E, manganese, zinc, copper, iron, selenium, and gamma linolenic acid (an essential fatty acid). Blue-green algae, such as *Aphanizomenon flos aquae* (AFA) or *Spirulina* (*Arthrospira*) have up about 62% amino acids in their extracts. Because extracts are a rich source of protein and other nutrients, they have been used in nutritional supplements.

Blue-green algae, such as AFA or *Spirulina* (*Arthrospira*), can be isolated from any source. The source can be a naturally occurring source that rich in blue-green algae. The source can also be a man-made source, such as an artificial lake or water source. The source can also be bioreactors or fermentors. The source can be an environment produced to grow and harvest blue-green algae commercially.

The blue-green algae extracts can include an extract from the whole alga or any part of the alga. The extract can be fractionated. The extract of blue-green algae can include any fraction, or isolated or purified molecule from a blue-green alga cell. The blue-green algae are disrupted, an inorganic or organic solvent is added, and extract (or molecules) is collected. Specific, non-limiting examples of extract are isolated using high performance liquid chromatography, thin layer chromatography, affinity column, magnetic beads or distillation. In one embodiment, fractionation is used to isolate the extract based on the molecular weight or the hydrophobicity of the molecules of the blue-green algae. For example, the extract can include those molecules of less than about 50 kDa, and not 50 kDa or greater; less than about 10 kDa, and not 10 kDa or greater; or less than about 5 kDa, and not 5 kDa or greater.

An extract of blue-green algae, such as a dried form, include about 0.5% to about 5% blue-green algae extract weight content of the composition. The range of blue-green algae extract in the composition can be from about 0.1% to about 20%, about 0.5% to about 20%, about 0.5% to about 10%, about 0.5% to about 5%, and about 0.5% to about 1% weight content of the composition. In other embodiments, the composition includes at least about 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, or more blue-green algae extract weight content. In an exemplary embodiment, blue-green algae extract is in range of about 0.1% to about 10% of the composition.

Red Algae Extracts

The compositions provided may include extracts from red algae. Red algae contain sulfated polysaccharides with D-galactoses bonded alternatively by alpha (1-3) and beta (1-4) bonds. These galactose-based polysaccharides are distinguished by the presence or not of a 3,6 anhydrous bridge on the alpha bonded (1-3) galactose residue and by their level of sulfation. Carrageenan is a generic term for the linear or branched sulfated galactose-based polysaccharides extracted from red algae (rhodophyceae or red seaweed). Examples in this case are described in WO/2009/027057.

Methods of galactose-based polysaccharide or carrageenan extraction and production can be derived from wild-grown red algae, like carrageenan-containing plants such as *Gigartina radula, Gigartina skottsbergii, Gigartina chamissoi, Gigartina stellata, Iridaea cordata, Chondrus chrispus* and *Sarcothalia crispate* seeded along nylon ropes and harvested in massive aqua-culture farming operations or obtained from synthetic carrageenan production. Isolation of the galactose-based polysaccharides from the red algae is conducted in accordance with standard techniques, as described in U.S. Pat. No. 3,094,517 to Stanley et al. The carrageenan is extracted from the cleaned algae while also being subjected to alkali modification by placing the algae in a solution made slightly alkaline by the addition of a low concentration of alkali salt (i.e., a pH of the solution is raised to a range of, e.g., 9-10) and then heating this solution to a temperature of around 80° C. for a period of time of about 20 minutes to as long as two hours.

There exist more than 10 structurally different carrageenans, their nature depending on the algae genus from which they are extracted. The three main types are iota-, kappa- and lambda-carrageenan, which differ slightly in their structure and degree of sulfation. Iota-carrageenan is a soft-gel forming sulfated galactose-based polysaccharide predominantly extracted from red seaweed, *Gigartina stellata* and *Chondrus crispus*. Kappa-carrageenan yields strong, rigid gels and is predominantly produced from *Kappaphycus cottonii*. Lambda-carrageenan, which is the most common form, is frequently used to thicken dairy products.

The galactose-based polysaccharides can have a molecular weight ranging from about 15 kDa to 5 MDa, and fractions having average molecular weights of more than 50 kDa, and especially fractions having average molecular weights in the range of from 50 kDa to 3 MDa.

The galactose-based polysaccharides also include carrageenans described in patent application WO/2009/027057, see for example for relevant information.

In one embodiment, compositions include about 0.1% to about 10% galactose-based polysaccharide or carrageenan weight content of the composition. The range of galactose-based polysaccharide or carrageenan in the composition can be from about 0.1% to about 20%, about 0.1% to about 10%, about 0.1% to about 5%, and about 0.1% to about 1% weight content of the composition. In other embodiments, the composition includes at least about 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, or more galactose-based polysaccharide or carrageenan weight content.

Algae Extraction

As provided herein, algae extracts can be prepared from fresh, dehydrated, or preserved algae or marine cells. The algae can be extracted in any aqueous solution, such as with water or a suitable buffered salt solution, or other solvents, such as ethanol and methanol, and DMSO. The extract may also be produced by any other suitable method. Following extraction, the extracts are dried, as described above. The algae extracts can be used directly, or can be stored as liquid, frozen liquid, dehydrated, freeze-dried, vacuum dried, drum dried cells and spray-dried cells.

In one embodiment, the extracts are filtered to separate fractions of different sizes. The filtration can be performed using ultra filtration filters having different molecular weight cut-offs, such as a filter with a 10 MDa cut-off that allows collection of molecules of less than about 10 MDa, and excludes molecules of about 10 MDa or greater. In this context, "about" refers to a difference of 5 kDa. In other examples, the molecular weight cut-off filter allows collection of molecules that are less than 5 MDa, and excludes molecules of 5 MDa or greater; less than 1 MDa, and excludes molecules of 1 MDa or greater; less than 500 kDa, and excludes molecules of 500 kDa or greater; less than 300 kDa, and excludes molecules of 300 kDa or greater; less than 100 kDa, and excludes molecules of 100 kDa or greater; or less than 50 kDa, and excludes molecules of 50 kDa or greater.

Other Components

The compositions provided herein can include one or more additional components. Non-limiting examples of additional components/agents optionally included in the composition include cooling agents such as menthol, warming agents, flavoring agents, salivating agents, tea extract, exogenous salts (e.g. Dead Sea salts), anti-septic and antibacterial agents, amino acids, essential oils, vitamin(s) (e.g., Vitamin A, Vitamin C, Vitamin B, and/or Vitamin D), carotenoid, rosemary, rosemary extract, caffeic acid, coffee extract, tumeric extract, curcumin, blueberry extract, grape seed extract, rosemaric acid, antioxidant, enzyme, prebiotic, probiotic, andrographis extract, 1-tryptophan, *Allium sativum*, herbal remedies, supplements, natural ingredients, minerals, energy boosting ingredients, sleep aids, immune system boosting agents, colorant, preservative, fragrance, fruit extract, others agents, and combinations thereof. Further potential additional components include hydrating agents.

Essential oils can be added to represent characteristically scented, essential herbal active agents, which can be disinfecting or impart antimicrobial action. Lemon oil, *eucalyptus* oil, balm oil, mint oil, camphor, aniseed oil, rosemary oil, spearmint oil, peppermint oil, *thymus* oil and sage oil can be used as essential oils. The concentration of the essential oils can be, approximately, 0.01 mg to 50 mg, in particular 0.05 mg to 15 mg per 10 ml, whereby 0.01 mg to 10 mg, in particular, 0.01 mg to 5 mg is lemon oil; 0.01 mg to 10 mg, in particular, 0.01 mg to 5 mg is *eucalyptus* oil; 0.01 mg to 5 mg, in particular, 0.01 mg to 0.3 mg is balm oil; 0.01 mg to 10 mg, in particular, 0.01 mg to 3 mg is mint oil; 0.01 mg to 10 mg, in particular, 0.01 mg to 3 mg is campho; 0.001 mg to 5 mg, in particular, 0.001 mg to 0.5 mg is aniseed oil; 0.001 mg to 5 mg, in particular, 0.001 mg to 0.05 mg is rosemary oil; 0.01 mg to 10 mg, in particular, 0.01 mg to 5 mg is spearmint oil; 0.01 mg to 10 mg, in particular, 0.01 mg to 5 mg is peppermint oil; 0.01 mg to 10 mg, in particular, 0.01 mg to 5 mg is *thymus* oil; and 0.001 mg to 5 mg, in particular, 0.001 mg to 0.5 mg is sage oil per 10 ml of the composition.

The composition can include a pharmaceutically acceptable carrier, e.g., one or more solvents, dispersion media, coatings, antimicrobial agents, isotonic and absorption delaying agents, and the like, compatible with administration to a mammal, such as a human. Any carrier compatible with the excipient(s) and therapeutic agent(s) is suitable for use. Supplementary active compounds may also be incorporated into the compositions.

Any antimicrobial agent known in the art can be used in the compositions at concentrations generally used for such agents. Antimicrobial agents include antibacterials, antifungals, and antivirals. Exemplary antibiotics (i.e., antibacterial agents) include the penicillins (e.g., penicillin G, ampicillin, methicillin, oxacillin, and amoxicillin), the cephalosporins (e.g., cefadroxil, ceforanid, cefotaxime, and ceftriaxone), the tetracyclines (e.g., doxycycline, minocycline, and tetracycline), the aminoglycosides (e.g., amikacin, gentamycin, kanamycin, neomycin, streptomycin, and tobramycin), the macrolides (e.g., azithromycin, clarithromycin, and erythromycin), the fluoroquinolones (e.g., ciprofloxacin, lomefloxacin, levofloxacin and norfloxacin), and other antibiotics including chloramphenicol, clindamycin, cycloserine, isoniazid, rifampin, sulfamethoxazole with trimethoprim, cefuroxime, cefpodoxime, and vancomycin. Antiviral agents are substances capable of inhibiting the replication of viruses. Examples of anti-viral agents include 1-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir. Antifungal agents include both fungicidal and fungistatic agents such as, for example, benzoic acid, undecylenic alkanolamide, ciclopirox olamine, polyenes, imidazoles, allylamine, thicarbamates, amphotericin B, butylparaben, clindamycin, econaxole, fluconazole, flucytosine, griseofulvin, nystatin, and ketoconazole.

The composition can also be formulated in combination with other agents typically used to relieve symptoms of sinusitis, hay fever, nasal congestion, allergic rhinitis, and/or non-allergic (perennial) rhinitis. Examples of other agents can include but are not limited to corticosteroids, other steroidal compounds, anti-histamines, decongestants, bronchodilators, β2-adrenergic agonists, and antimicrobial agent. In one embodiment, the composition further includes at least one of a corticosteroid, other steroidal compound, antihistamine, decongestant, bronchodilator, β2-adrenergic agonist, and antimicrobial agent.

Corticosteroids and other steroidal compounds can be used with the described composition to reduce inflammation and histamine production in the nasal passages, thereby relieving nasal congestion, runny nose, sneezing, sinus pain, headaches etc. Examples of corticosteroids and other steroidal compounds can include alcometasone, beclomethasone, betamethasone, budesonide, ciclesonide, clobetasol, deflazacort, diflucortolone, desoxymethasone, dexamethasone, fludrocortisone, flunisolide, fluocinolone, fluometholone, fluticasone, hydrocortisone, mometasone furoate, nandrolone decanoate, rimexolone, methylprednisolone, prednisolone and triamcinolone acetonide. Exemplary examples of corticosteroids and other steroidal compounds can include mometasone, budesonide, fluticasone, flunisolide, beclomethasone, triamcinolone, and ciclesonide.

Antihistamines are one of the primary medicaments employed to treat allergic rhinitis. Antihistamines are helpful to control sneezing, itching, and rhinorrhea, as well as associated ocular symptoms, but are ineffective in relieving nasal blockage. Antihistamines compete with histamine for binding to H1 receptors and thereby prevent the action of histamine which includes bronchospasm, edema, increased mucus secretion and itching. The antihistamines used today can be given orally or topically (intranasally). Examples of useful antihistamines that may be used with the described composition can include acrivastine, azatadine, azelastine, astemizole, brompheniramine, carbinoxamine, cetirizine, chlorpheniramine, clemastine, cyproheptadine, dexchlorpheniramine, diphenhydramine, doxylamine, ebastine, hydroxyzine, ketotifen, levocabastine, lodoxamide, loratadine, meclizine, mequitazine, methdilazine, oxatomide, phenindamine, promethazine, pyrilamine, setastine, rocastine, tazifylline, temelastine, terfenadine, trimeprazine, tripelennamine, and triprolidine. Exemplary examples of anti-histamines can include astemizole, Azatadine, azelastine, cetirizine, ebastine, ketotifen levocabastine, loratadine, lodoxamide, levocabastine, mequitazine, oxatomide, setastine, tazifylline, temelastine, and terfenadine.

Nasal decongestants include compounds that relieve nasal congestion by narrowing (constricting) the blood vessels and reducing blood flow, swelling and mucous formation. The vast majority of decongestants act via enhancing norepinephrine (noradrenaline) and epinephrine (adrenaline) or adrenergic activity by stimulating the α-adrenergic receptors. Decongestants can be oral (e.g. tablets) in nasal sprays or drops. Examples of decongestants can include ephedrine, levo-methamphetamine, naphazoline, oxymetazolin, phenylephrine, phenylpropanolamine, propylhexedrine, pseudoephedrine, synephrin, tetrahydrozoline, tramazoline, and xylometazoline.

Bronchodilators are substances that dilate the bronchi and bronchioles, thereby decreasing resistance in the respiratory airway and increasing airflow to the lungs. They are most useful in obstructive lung diseases, of which asthma and chronic obstructive pulmonary disease are the most common conditions. Classes within this category of compounds include β2-adrenergic agonists and anticholinergics. β2-adrenergic agonists, also known as β2-adrenergic receptor agonists, are a class of drugs that act on the β2-adrenergic receptor, thereby causing smooth muscle relaxation, resulting in dilation of bronchial passages. Examples of long-acting β2-agonists (LABAs) include formoterol, salmeterol and salts thereof, such as formoterol fumarate and salmeterol xinafoate. Examples of short-acting β2-agonists include salbutamol, terbutaline and salts thereof such as salbutamol sulfate. Examples of anticolinergics include agents used in COPD and/or asthma such as tiotropium and ipratropium bromide.

Plant extracts that can be used in the composition include in a non-limiting manner extracts isolated by various means (e.g. via extraction with aqueous or organic solvents) by different parts of the plant (e.g. root, fruits, leaves etc) such as rosemary extract, coffee extract, tumeric extract, blueberry extract, grape seed extract, andrographis extract, *Allium sativum* extract, Thyme extract (e.g, extract of *Thymus vulgaris*), *Centella asiatica* extract or extracts typically used in cosmetic and pharmaceutical industry such as those included in Pharmacopoeia, WHO (World Health Organization) monographs or in the compendium PDR for Herbal Medicines 4$^{th}$ Edition (Thomson Healthcare). Typical concentrations of plant extracts that could be used in the composition range between 0.001% to 5%, most preferably between 0.05-1% in the composition.

Herbal remedies and other natural ingredients (e.g. carotenoids, caffeic acid, rosemaric acid, curcumin) can also be included.

A further optional component that can be included in the composition is a hydrating agent. Hydrating agents can be defined as agents that improve stratum corneum hydration, reduce transepidermal water loss, maintain skin softness and elasticity or have a general soothing function in case of dryness and/or irritation. Examples of such hydrating agents include propylene glycol, glycerol, sorbitol, polyethylene glycol or other agents described in U.S. Pat. No. 5,603,943 or US 20070190081. Preferable hydrating agents include, dexpanthenol or panthothenic acid at a concentration ranging from 0.25-2.5% w/w, more preferably 0.5-1.5% w/w, more preferably 1% w/w, hyaluronic acid or a salt thereof (such as sodium hyaluronate) at a concentration ranging from 0.01-2.5% w/w preferably 0.025-0.5% w/w, more preferably 0.2% w/w or ectoin, a natural compound found in several species of bacteria such as Ectothiorhodospira halochloris, at a concentration ranging from 0.001 to 10% w/w, preferably 0.01-2% w/w, more preferably 0.5-1% w/w.

Respiratory Tract and Respiratory Mucosal-Related Conditions

The methods and compositions of the invention are useful for the treatment of respiratory tract and/or respiratory mucosal-related conditions. Respiratory tract and respiratory mucosal-related conditions include any conditions or disorders with abnormal mucus production, secretion or clearance or inflammation (bacterial, viral, allergic or autoimmune) of the nasal, bronchial and pulmonary mucosa. Examples of diseases include acute rhinosinusitis, recurrent acute rhinosinusitis, subacute rhinosinusitis, chronic rhinosinusitis, acute exacerbation of chronic rhinosinusitis, sinusitis, allergic and non-allergic rhinitis, asthma, cystic fibrosis, chronic obstructive pulmonary disease (COPD), and other diseases of the upper and lower respiratory tract.

The principal functions of the nasal passages are the regulation of the inspiratory air flow, the heating and humidification of inspired air and the elimination of foreign elements (dust, microbial germs). The ciliate epithelium, which covers the nasal mucosa, plays a vital role in its defense from infections. The vibratile cilia of this epithelium are immersed in protective mucus, which surrounds them, and their purpose is to push this mucous, together with any external impurities, posteriorly, i.e. towards the pharynx, by their motions.

Rhinosinusitis is the inflammation (bacterial, viral, allergic or autoimmune) of the paranasal sinuses. Rhinosinusitis can be classified into several categories: Acute rhinosinusitis—a new infection that may last up to four weeks and can be subdivided symptomatically into severe and non-severe; Recurrent acute rhinosinusitis—four or more separate episodes of acute sinusitis that occur within one year; Subacute rhinosinusitis—an infection that lasts between four and 12 weeks, and represents a transition between acute and chronic infection; Chronic rhinosinusitis—when the signs and symptoms last for more than 12 weeks; and Acute exacerbation of chronic rhinosinusitis—when the signs and symptoms of chronic rhinosinusitis exacerbate, but return to baseline after treatment. Symptoms of rhinosinusitis include nasal congestion, facial pain, headache, fever, and general malaise. Some nonlimiting examples of inflammatory conditions would include: acute and chronic rhinosinusitis, allergic and non-allergic rhinitis, asthma, cystic fibrosis, chronic obstructive pulmonary disease (COPD), other diseases of the respiratory tract.

There are several paired paranasal sinuses, including the frontal, ethmoidal, maxillary and sphenoidal sinuses. Rhinosinusitis often occurs as part of a spectrum of diseases that affect the respiratory tract and respiratory mucosal-related conditions are often linked to other conditions, such as asthma or cystic fibrosis. All forms of rhinosinusitis may either result in, or be a part of, a generalized inflammation of the airway, so other airway symptoms, such as cough, may be associated with it.

Pharmaceutical Compositions

The compositions provided herein are also useful as pharmaceutical compositions for treatment of respiratory tract and/or respiratory mucosal-related conditions, such as rhinosinusitis. Pharmaceutical compositions can include a pharmaceutically acceptable carrier or adjuvant or can be provided without such a carrier or adjuvant. In one embodiment, the pharmaceutical composition includes an ionic aqueous solution, an extract from brown algae, and a pharmaceutically acceptable carrier or adjuvant. In another embodiment, the pharmaceutical composition includes an ionic aqueous solution, a branched, sulfated polysaccharide having an average molecular weight greater than 4 kDa and comprising L-fucose and sulfate ester groups and a pharmaceutically acceptable carrier or adjuvant. The pharmaceutically acceptable carriers or adjuvants useful are conventional. Remington's Pharmaceutical Sciences, by E. W. Martin, Mack Publishing Co., Easton, Pa., 15th Edition (1975), describes compositions and compositions suitable for pharmaceutical delivery are described herein.

The composition may be contained in any appropriate amount in any suitable carrier substance, and is generally present in an amount of 1-99% by weight of the total weight of the pharmaceutical composition. Pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

An exemplary embodiment of a composition for nasal administration can include a seawater/saline solution exhibiting an osmolarity value ranging from 250-350 mOsm/L for isotonic, >350 mOsm/L for hypertonic and <250 mOsm/L for hypotonic corresponding to a 10 to about 99.9% weight content within the aqueous solution [the corresponding NaCl contents are 0.9%, >0.9% and <0.9% NaCl or NaCl equivalents], a branched, sulfated polysaccharide having an average molecular weight greater than 4 kDa with L-fucose and sulfate ester groups, and optionally, any or both of a blue/green algae extract and a galactose-based polysaccharide such as a carrageenan.

Another exemplary embodiment of a composition for nasal administration can include seawater/saline solution, an extract from brown algae, and blue/green algae extract such as *Spirulina*, and, optionally, a red algae extract such as carrageenan.

In certain embodiments, the composition can be packaged in a pressurized container, equipped with an auto-sterilizing nozzle, with instructions for use.

Methods of Delivery

Pharmaceutical compositions described above can be delivered via different methodologies including sprays, irrigation systems (e.g. neti pot), syringes or others. The composition may be provided in a dosage form that is suitable for a nasal aerosol or inhalation administration route. An exemplary method of administration of the composition can include spraying vaporized or nebulized disseminated microparticles under an active dynamic pressure.

Suitable aerosol dispensers for use will be apparent to those skilled in the art, and may vary from simple devices analogous to perfume dispensers to pressurized spray cans and even complex apparatus such as might be used in hospitals. Whichever device is used it is generally preferable that it comprises some kind of dosimeter to control the amount of solution administered in one go. One device, which corresponds to a dispenser with a nozzle, effectively incorporates such a dosimeter without any specialized adaptation being necessary, the limit stop of the depressible spray head fixing the maximum single amount of solution dispensable at once. Specially developed spray devices may be made with a hand-held device comprising a reservoir of the composition.

Suitable means for dispersing the spray, preferably in aerosol form, are provided. Examples include pneumatically pressurized devices and devices employing pressurized gas forced across the opening of a tube leading into the reservoir to create an aerosol, and press-button type devices wherein the button, when pressed, creates pressure on the surface of the liquid in the reservoir, forcing it up through a tube and through a fine nozzle to disperse the solution into an aerosol spray. Other examples include aerosol dispensers, inhalers, pump sprayers, nebulizers (such as positive pressure nebulizers), and the like. In some embodiments, the device used is pre-filled with a composition described herein.

One embodiment would include a multi-dose metered dose spray pump allowing for spraying of a fixed volume of solution. Alternatively, gas driven (e.g. nitrogen) devices, such as systems that hold the composition separate from the propellant in aluminum or plastic (or any other type of) bottle. These devices deliver solution at variable diffusion flows and angles when combined with different actuators. Preferred diffusion flows could deliver 0.5-10 ml solution per spraying second at angles of 0-60° C.

The compositions described above can be administered as per physician's instructions and depending on the condition. A preferred mode of (nasal) administration would comprise 1-5 sprays per nostril, 1-5 times daily; this could extend to many weeks depending on the condition or symptom to be treated (e.g. in allergy).

Treatment

The methods described herein provide for treating respiratory tract and/or respiratory mucosa-related conditions or symptoms thereof that include acute and chronic rhinosinusitis, sinusitis, allergic and non-allergic rhinitis, asthma, cystic fibrosis, chronic obstructive pulmonary disease (COPD), and other diseases of the upper and lower respiratory tract. In one embodiment, methods include treating a respiratory tract and/or respiratory mucosa-related condition in a subject in need thereof, by aerosolizing a pharmaceutical composition in a nasal passageway of the subject. Such methods include the step of administering to the subject a therapeutic amount a composition herein sufficient to treat rhinosinusitis, e.g., acute and chronic rhinosinusitis, sinusitis, allergic and non-allergic rhinitis, asthma, cystic fibrosis, chronic obstructive pulmonary disease (COPD), and other diseases of the respiratory tract.

The methods and compositions described herein can be administered in combination with one or more agents or separately as successive treatments. For example, one embodiment describes the composition administered in combination as a single treatment with at least one of a corticosteroid, other steroidal compound, anti-histamine, decongestant, bronchodilator, β2-adrenergic agonist, and antimicrobial agent. In another embodiment, the composition is administered as an independent treatment with another, successive treatment including at least one of a corticosteroid, other steroidal compound, anti-histamine, decongestant, bronchodilator, β2-adrenergic agonist, and antimicrobial agent.

It will be appreciated that, although not precluded, treating rhinosinusitis does not require that rhinosinusitis or symptoms associated therewith be completely eliminated.

The therapeutic methods described herein (that include prophylactic treatment) in general comprise administration of a therapeutically effective amount of the compositions herein to a subject (e.g., animal, human) in need thereof, including a mammal, particularly a human. Such treatment will be suitably administered to subjects, particularly humans, suffering from, having, susceptible to, or at risk for rhinosinusitis or inflammatory condition, or symptom thereof. Determination of those subjects "at risk" can be made by any objective or subjective determination by a diagnostic test or opinion of a subject or health care provider.

In addition to standard methods of pharmaceutical chemistry and formulations described above, the practice of the compositions and methods described herein can employ, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

EXAMPLES

The following examples are put forth so as to provide those of ordinary skill in the art with a complete disclosure and description of how to make and use the assay, screening, and therapeutic methods of the invention, and are not intended to limit the scope of what the inventors regard as their invention.

Figure 1:
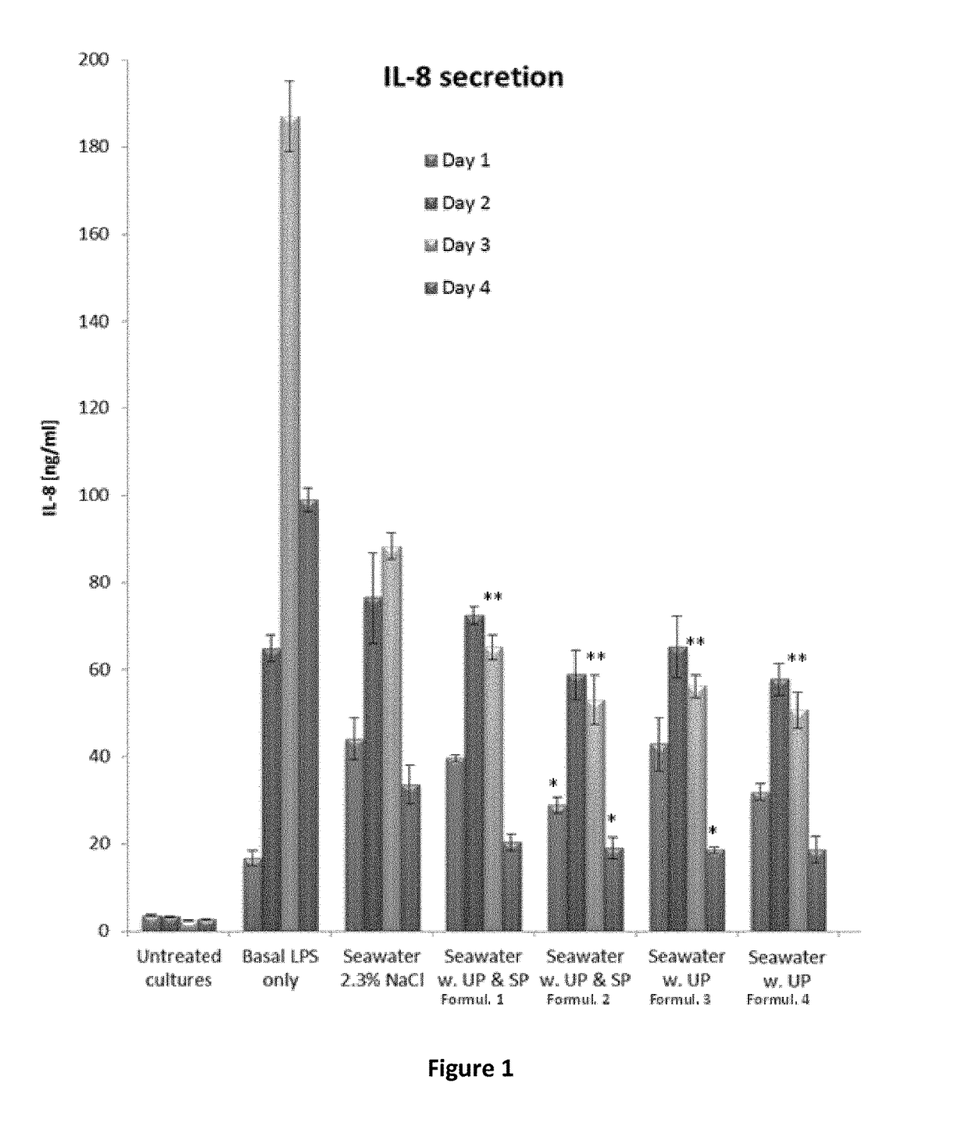
FIG. 1 presents data obtained after testing Formulations 1-4 and various controls for IL-8 secretion in a three-dimensional reconstituted human airway epithelia model utilizing cells isolated from normal human donors (see Example 1).

Example 1: Formulations of the Invention are Capable of Reducing Inflammatory Marker Secretion FIG. 1 presents data obtained with solutions described in Formulations 1-4 in a three-dimensional reconstituted human airway epithelia model (commercially available by Epithelix, Geneva, CH). The airway epithelia are freshly isolated from nasal biopsies and fully differentiated. Due to the cells differentiated nature and properties, the model is considered a highly physiological system to study effects of applied agents including cytotoxicity and inflammation. Thus, in the experiment presented in FIG. 1, fully differentiated human nasal epithelial cells were reconstituted with a mixture of cells isolated from nasal polyps of 14 different normal donors in three-dimensional cultures closely resembling natural nasal tissues (Huang S et al, The Use of In Vitro 3D Cell Models in Drug Development for Respiratory Diseases, InTech. 2011 ISBN: 978-953-307-615-7). Each patient cell insert used was washed apically with culture medium 3 days before the experiment to remove accumulated mucous and to minimize the risk of interference with the tests. To verify that all selected inserts satisfy appropriate quality controls prior to use of test agents, inserts were inspected under the microscope to verify proper function of the cilia and relevant Trans-Epithelial Electrical Resistance (TEER). Subsequently, LPS was added to the culture medium at 0.3 mg/ml in the presence or absence of different solutions (10 µl applied apicaly two times a day within 8 hours) for a total of four days. Culture medium was collected at days 0, 1, 2, 3 and 4 and IL-8, a well-established inflammatory marker secreted by airway epithelial cells, was measured by ELISA.

As expected, untreated cultures did not show any significant change of IL-8 release. LPS greatly stimulated the IL-8 expression in a time-dependent manner, with a peak at Day 3. A hypertonic seawater solution comprising 2.3% NaCl was capable of reducing the IL-8 release caused by LPS. Interestingly, solutions comprising seawater 2.3% NaCl and indicated ingredients (UP: *Undaria pinnafitida* extract, SP: *Spirulina platensis* extract) (Formulations 1-4) were superior to seawater 2.3% NaCl alone (*$p<0.05$, **$p<0.01$, Student's t-test) indicating that algae ingredients potentiate the effect of seawater 2.3% NaCl in a statistically significant manner. It is noted that all tested solutions were not cytotoxic to the cultured cells (as measured by lack of LDH release in the medium).

Example 2: Formulations of the Invention Reduce Inflammation and Improve Nasal Cell Function in Cultured Epithelial Cells from an Allergic Donor In the experiments presented in FIG. 2, fully differentiated human nasal epithelial cells were reconstituted with a mixture of inserts derived from an allergic donor (female, 35 years old) in three-dimensional cultures closely resembling natural nasal tissues (Huang S et al, The Use of In Vitro 3D Cell Models in Drug Development for Respiratory Diseases, InTech. 2011 ISBN: 978-953-307-615-7). Cells were washed apically with culture medium 3 days before the experiment to remove accumulated mucus and to minimize the risk of interference with the tests. Microscopic analysis of cells and relevant Trans-Epithelial Electrical Resistance (TEER) measurements confirmed proper function of the cilia prior to the initiation of the experiment.

Figure 2:
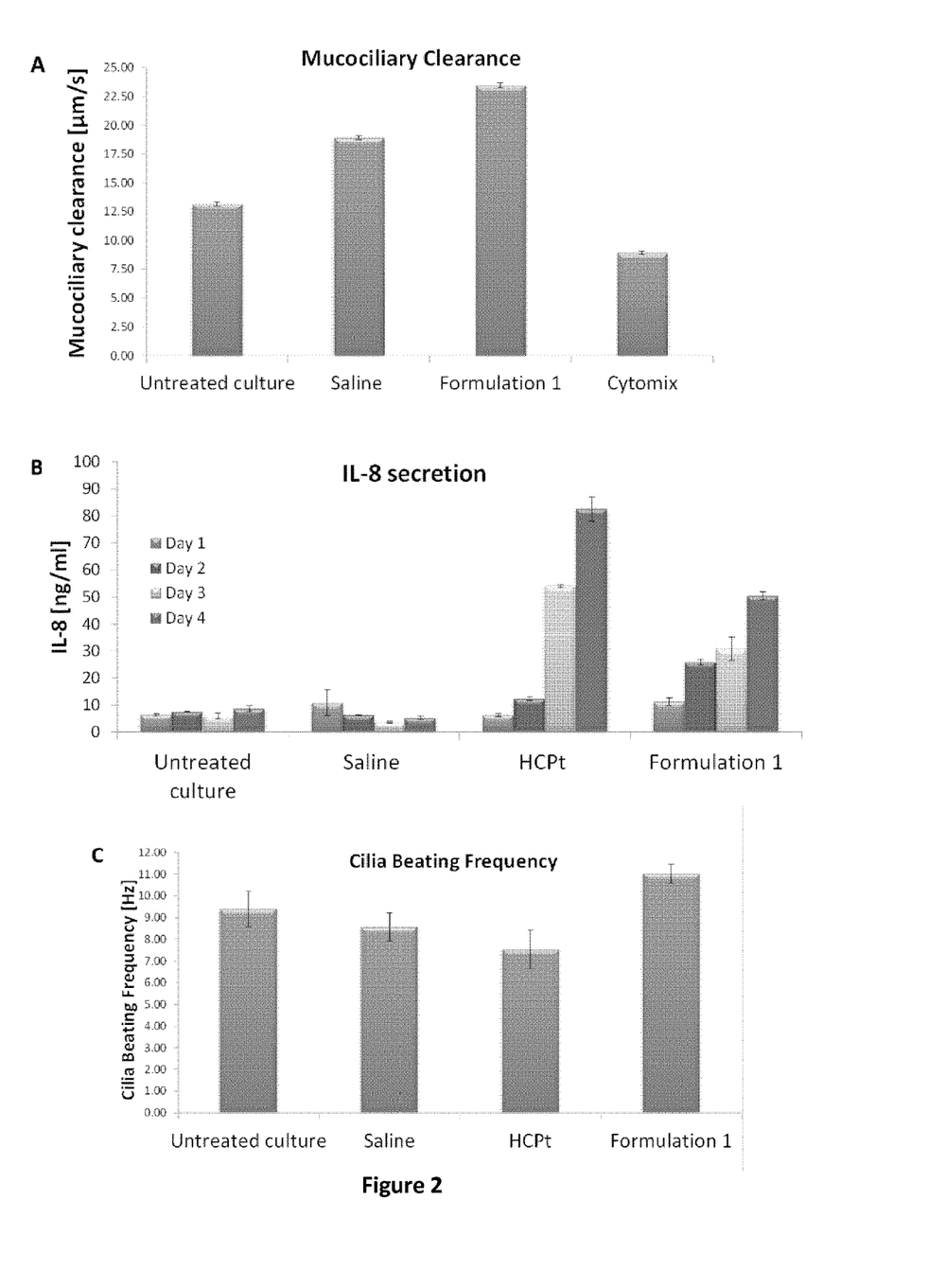
FIG. 2 presents data obtained after testing Formulation 1 and various controls for mucociliary clearance (Plate A), IL-8 secretion (Plate B) and cilia beating frequency (Plate C) in a three-dimensional reconstituted human airway epithelia model utilizing cells isolated from a human allergic donor (see Example 2).

The experimental design following the aforementioned cell preparation was as follows: At Day 0, cells were left untreated (negative control) or were treated with 10 µl of Formulation 1, saline control or Cytomix (a mixture of IL-1beta, TNF-alpha and IFN-gamma predicted to exert cytotoxic effects to the nasal epithelium) applied onto the apical surface of the epithelium. 24 hours later (Day 1), the effect of solutions on Mucociliary Clearance (MCC) was monitored using a Ds-5mc camera (Nikon) connected to a DMIRE2 microscope (Leica). Specifically, 5 µM microbeads were added at the apical surface of cell cultures as these were incubated with Formulation 1 (or saline control) and 1 minute movies showing the movement of beads were taken. Subsequent analyses using the imaging software Image Pro Plus (Mediacy) tracked movements of beads and velocity of each particle was calculated in order to determine the speed of MCC (in µM/sec). Following MCC measurements, 30 µl of 20 mM HCPt (Ammonium hexachloroplatinate; a strong respiratory sensitizer) or saline was added to cells in the presence of Formulation 1 or saline control. After 16 hours of exposure (Day 2), HCPt solutions were removed and new cell culture medium containing Formulation 1 or saline control was added to cells. Treatments with solutions continued twice daily throughout Day 2 and in Day 3; solutions were removed during at Day 4 (replaced with cell culture medium). During this time (Days 1-4), culture media was collected for analysis of inflammatory marker IL-8 by ELISA. At Day 4, cilia beating frequency (CBF) measurements (expressed as Hz) were conducted by a dedicated setup including a camera (Sony XCD V60 Firewire), a PCI card and relevant software.

FIG. 2, panel A, shows that Formulation 1 significantly increased mucociliary clearance in comparison to saline (results represents an average value of 200-500 particles tracked). As expected Cytomix had a detrimental effect on the nasal epithelium that resulted in significant reduction of MCC versus baseline. Panel B presents IL-8 secretion data at Days 1-4. As expected, HCPt efficiently induced inflammation with a peak of IL-8 secretion at Day 4. No IL-8 secretion was observed in cells receiving saline instead of HCPt or in untreated cultures. Formulation 1 was capable of reducing inflammation induced by respiratory allergen HCPt in these three dimensional cultures from an allergic donor. Panel C shows CBF measurements at Day 4. As expected cell cultures treated with HCPt had an impaired function as measured by reduced CBF versus control. On the contrary, cultures treated with HCPt that have received Formulation 1 had increased CBF values in agreement with protective properties observed in the IL-8 analyses and the improved function exerted on MCC. Overall, these results suggest that Formulation 1 improves nasal function parameters in three dimensional cultures of cell islets generated by an allergic donor and reduces inflammation induced by a respiratory allergen. It is noted that specific measurements of LDH release (in the culture medium) conducted during the course of these experiments, proved that Formulation 1 was not cytotoxic to cultured cells (data not shown).

Example 3: Materials and Methods

The following example formulations may be prepared:
Formulation 1
A seawater solution comprising:

| | |
|---|---|
| Seawater | 71.6 g |
| *Undaria pinnafitida* extract | 0.1 g |
| *Spirulina platensis* extract | 0.5 g |
| Purified/distilled/filtered water | q.s. 100.0 g |

Formulation 2
A seawater solution comprising:

| | |
|---|---|
| Seawater | 71.6 g |
| *Undaria pinnafitida* extract | 0.3 g |
| *Spirulina platensis* extract | 0.5 g |
| Purified/distilled/filtered water | q.s. 100.0 g |

Formulation 3
A seawater solution comprising:

| | |
|---|---|
| Seawater | 71.6 g |
| *Undaria pinnafitida* extract | 0.1 g |
| Purified/distilled/filtered water | q.s. 100.0 g |

Formulation 4

A seawater solution comprising:

| | |
|---|---|
| Seawater | 71.6 g |
| Undaria pinnafitida extract | 0.3 g |
| Purified/distilled/filtered water | q.s. 100.0 g |

Formulation 5

A seawater solution comprising:

| | |
|---|---|
| Seawater | 71.6 g |
| Undaria pinnafitida extract | 0.3 g |
| Spirulina platensis extract | 0.5 g |
| Iota-Carrageenan | 0.16 g |
| Purified/distilled/filtered water | q.s. 100.0 g |

Formulation 6

A seawater solution comprising:

| | |
|---|---|
| Seawater | 71.6 g |
| Undaria pinnafitida extract | 0.1 g |
| Spirulina platensis extract | 0.5 g |
| Iota-Carrageenan | 0.16 g |
| Purified/distilled/filtered water | q.s. 100.0 g |

Formulation 7

A seawater solution comprising:

| | |
|---|---|
| Seawater | 71.6 g |
| Undaria pinnafitida extract | 0.1 g |
| Spirulina platensis extract | 0.5 g |
| Dexpanthenol | 1.0 g |
| Purified/distilled/filtered water | q.s. 100.0 g |

Formulation 8

A seawater solution comprising:

| | |
|---|---|
| Seawater | 71.6 g |
| Undaria pinnafitida extract | 0.3 g |
| Spirulina platensis extract | 0.5 g |
| Dexpanthenol | 1.0 g |
| Purified/distilled/filtered water | q.s. 100.0 g |

Formulation 9

A seawater solution comprising:

| | |
|---|---|
| Seawater | 71.6 g |
| Undaria pinnafitida extract | 0.1 g |
| Dexpanthenol | 1.0 g |
| Purified/distilled/filtered water | q.s. 100.0 g |

Formulation 10

A seawater solution comprising:

| | |
|---|---|
| Seawater | 71.6 g |
| Undaria pinnafitida extract | 0.3 g |
| Dexpanthenol | 1.0 g |
| Purified/distilled/filtered water | q.s. 100.0 g |

Formulation 11

A seawater solution comprising:

| | |
|---|---|
| Seawater | 71.6 g |
| Undaria pinnafitida extract | 0.1 g |
| Spirulina platensis extract | 0.5 g |
| Iota-Carrageenan | 0.16 g |
| Dexpanthenol | 1.0 g |
| Purified/distilled/filtered water | q.s. 100.0 g |

Formulation 12

A seawater solution comprising:

| | |
|---|---|
| Seawater | 71.6 g |
| Undaria pinnafitida extract | 0.3 g |
| Spirulina platensis extract | 0.5 g |
| Iota-Carrageenan | 0.16 g |
| Dexpanthenol | 1.0 g |
| Purified/distilled/filtered water | q.s. 100.0 g |

Formulations 1-12 result in hypertonic seawater solutions of approximately 2.2-2.5% NaCl.

Formulation 13

A seawater solution comprising:

| | |
|---|---|
| Seawater | 28.6 g |
| Undaria pinnafitida extract | 0.1 g |
| Spirulina platensis extract | 0.5 g |
| Purified/distilled/filtered water | q.s. 100.0 g |

Formulation 14

A seawater solution comprising:

| | |
|---|---|
| Seawater | 28.6 g |
| Undaria pinnafitida extract | 0.3 g |
| Spirulina platensis extract | 0.5 g |
| Purified/distilled/filtered water | q.s. 100.0 g |

Formulation 15

A seawater solution comprising:

| | |
|---|---|
| Seawater | 28.6 g |
| Undaria pinnafitida extract | 0.3 g |
| Spirulina platensis extract | 0.5 g |
| Iota-Carrageenan | 0.16 g |
| Purified/distilled/filtered water | q.s. 100.0 g |

Formulation 16

A seawater solution comprising:

| | |
|---|---|
| Seawater | 28.6 g |
| Undaria pinnafitida extract | 1.0 g |
| Spirulina platensis extract | 0.5 g |
| Dexpanthenol | 1.0 g |
| Purified/distilled/filtered water | q.s. 100.0 g |

Formulation 17

A seawater solution comprising:

| | |
|---|---|
| Seawater | 28.6 g |
| Undaria pinnafitida extract | 0.3 g |
| Spirulina platensis extract | 0.5 g |

-continued

| | |
|---|---|
| Dexpanthenol | 1.0 g |
| Purified/distilled/filtered water | q.s. 100.0 g |

Formulation 18
A seawater solution comprising:

| | |
|---|---|
| Seawater | 28.6 g |
| *Undaria pinnafitida* extract | 0.3 g |
| *Spirulina platensis* extract | 0.5 g |
| Iota-Carrageenan | 0.16 g |
| Dexpanthenol | 1.0 g |
| Purified/distilled/filtered water | q.s. 100.0 g |

Formulations 13-18 result in isotonic seawater solutions of approximately 0.9% NaCl
Preparation of Solutions of Formulations 1-18
Formulations 1-18 are made by charging in the mixer

| | |
|---|---|
| 71.6 or 28.6 g | of Seawater |
| 0.1 or 0.3 g | of *Undaria pinnafitida* extract |
| 0.5 g (or not) | of *Spirulina platensis* extract |
| 0.16 g (or not) | of Iota-Carrageenan |
| 1 g (or not) | of Dexpanthenol | and the remaining purified water and mix for 15 min until a clear, homogeneous solution is obtained.

Formulation 19
A seawater solution comprising:

| | |
|---|---|
| *Undaria pinnafitida* extract | 0.3 g |
| *Spirulina platensis* extract | 0.5 g |
| Seawater (electrodialyzed to 2.2% NaCl) | q.s. 100.0 g |

Formulation 20
A seawater solution comprising:

| | |
|---|---|
| *Undaria pinnafitida* extract | 0.3 g |
| Seawater (electrodialyzed to 2.2% NaCl) | q.s. 100.0 g |

Formulation 21
A seawater solution comprising:

| | |
|---|---|
| *Undaria pinnafitida* extract | 0.3 g |
| *Spirulina platensis* extract | 0.5 g |
| Iota-Carrageenan | 0.16 g |
| Seawater (electrodialyzed to 2.2% NaCl) | q.s. 100.0 g |

Formulation 22
A seawater solution comprising:

| | |
|---|---|
| *Undaria pinnafitida* extract | 0.3 g |
| *Spirulina platensis* extract | 0.5 g |
| Seawater (electrodialyzed to 0.9% NaCl) | q.s. 100.0 g |

Formulation 23
A seawater solution comprising:

| | |
|---|---|
| *Undaria pinnafitida* extract | 0.3 g |
| *Spirulina platensis* extract | 0.5 g |
| Iota-Carrageenan | 0.16 g |
| Seawater (electrodialyzed to 0.9% NaCl) | q.s. 100.0 g |

Formulation 24
A seawater solution comprising:

| | |
|---|---|
| *Undaria pinnafitida* extract | 0.3 g |
| *Spirulina platensis* extract | 0.5 g |
| Dexpanthenol | 1.0 g |
| Seawater (electrodialyzed to 2.2% NaCl) | q.s. 100.0 g |

Formulation 25
A seawater solution comprising:

| | |
|---|---|
| *Undaria pinnafitida* extract | 0.3 g |
| Dexpanthenol | 1.0 g |
| Seawater (electrodialyzed to 2.2% NaCl) | q.s. 100.0 g |

Formulation 26
A seawater solution comprising:

| | |
|---|---|
| *Undaria pinnafitida* extract | 0.3 g |
| *Spirulina platensis* extract | 0.5 g |
| Iota-Carrageenan | 0.16 g |
| Dexpanthenol | 1.0 g |
| Seawater (electrodialyzed to 2.2% NaCl) | q.s. 100.0 g |

Formulation 27
A seawater solution comprising:

| | |
|---|---|
| *Undaria pinnafitida* extract | 0.3 g |
| *Spirulina platensis* extract | 0.5 g |
| Dexpanthenol | 1.0 g |
| Seawater (electrodialyzed to 0.9% NaCl) | q.s. 100.0 g |

Formulation 28
A seawater solution comprising:

| | |
|---|---|
| *Undaria pinnafitida* extract | 0.3 g |
| *Spirulina platensis* extract | 0.5 g |
| Iota-Carrageenan | 0.16 g |
| Dexpanthenol | 1.0 g |
| Seawater (electrodialyzed to 0.9% NaCl) | q.s. 100.0 g |

Preparation of Solutions of Formulations 19-28
Following the method of U.S. Pat. No. 6,451,352, these formulations may be prepared by electrodialyzing seawater to the desired osmotic content, then adding and mixing the additional ingredients. An alternative method is to mixing all the ingredients together and then electrodialyze.

Formulation 29
A seawater solution comprising:

| | |
|---|---|
| Seawater | 71.6 g |
| *Undaria pinnafitida* extract | 0.1 g |
| *Spirulina platensis* extract | 0.5 g |
| *Eucalyptus* oil | 0.0075 g |
| Spearmint oil | 0.015 g |
| Thyme extract | 0.1 g |

-continued

| | |
|---|---|
| 1,3 propanediol | 5 g |
| Glycerin | 3 gr |
| Purified/distilled/filtered water | q.s. 100.0 g |

Formulation 30

A seawater solution comprising:

| | |
|---|---|
| Seawater | 71.6 g |
| *Undaria pinnafitida* extract | 0.3 g |
| *Spirulina platensis* extract | 0.5 g |
| *Eucalyptus* oil | 0.0075 g |
| Spearmint oil | 0.015 g |
| Thyme extract | 0.1 g |
| 1,3 propanediol | 5 g |
| Glycerin | 3 gr |
| Purified/distilled/filtered water | q.s. 100.0 g |

Formulation 31

A seawater solution comprising:

| | |
|---|---|
| Seawater | 71.6 g |
| *Undaria pinnafitida* extract | 0.1 g |
| *Eucalyptus* oil | 0.0075 g |
| Spearmint oil | 0.015 g |
| Thyme extract | 0.1 g |
| 1,3 propanediol | 5 g |
| Glycerin | 3 gr |
| Purified/distilled/filtered water | q.s. 100.0 g |

Formulation 32

A seawater solution comprising:

| | |
|---|---|
| Seawater | 71.6 g |
| *Undaria pinnafitida* extract | 0.3 g |
| *Eucalyptus* oil | 0.0075 g |
| Spearmint oil | 0.015 g |
| Thyme extract | 0.1 g |
| 1,3 propanediol | 5 g |
| Glycerin | 3 gr |
| Purified/distilled/filtered water | q.s. 100.0 g |

Preparation of Solutions of Formulations 29-32

Formulations 29-32 are made by charging in the mixer the following ingredients to form a first mix:

| | |
|---|---|
| 71.6 or 28.6 g | of Seawater |
| 0.1 or 0.3 g | of *Undaria pinnafitida* extract |
| 0.5 g (or not) | of *Spirulina platensis* extract |
| 0.16 g (or not) | of Iota-Carrageenan |
| 0.1 g (or not) | of Thyme extract |

A second mix containing (in a small volume of purified water):

| | |
|---|---|
| 0.0075 g | of *Eucalyptus* oil |
| 0.015 g | of Spearmint oil |
| 5 gr | of 1,3 propanediol |

Then addition of glycerin in the 2$^{nd}$ mix:

| | |
|---|---|
| 3 gr | of Glycerin |

The second mix is then added to the first mix under continuous and intense stirring over 30 minutes and purified water is added to a final weight of 100 grams.

Formulation 33

A seawater solution comprising:

| | |
|---|---|
| *Undaria pinnafitida* extract | 0.1 g |
| *Spirulina platensis* extract | 0.5 g |
| *Eucalyptus* oil | 0.0075 g |
| Spearmint oil | 0.015 g |
| Thyme extract | 0.1 g |
| 1,3 propanediol | 5 g |
| Glycerin | 3 gr |
| Seawater (electrodialyzed to 2.2% NaCl) | q.s. 100.0 g |

Formulation 34

A seawater solution comprising:

| | |
|---|---|
| *Undaria pinnafitida* extract | 0.3 g |
| *Spirulina platensis* extract | 0.5 g |
| *Eucalyptus* oil | 0.0075 g |
| Spearmint oil | 0.015 g |
| Thyme extract | 0.1 g |
| 1,3 propanediol | 5 g |
| Glycerin | 3 gr |
| Seawater (electrodialyzed to 2.2% NaCl) | q.s. 100.0 g |

Formulation 35

A seawater solution comprising:

| | |
|---|---|
| *Undaria pinnafitida* extract | 0.1 g |
| *Eucalyptus* oil | 0.0075 g |
| Spearmint oil | 0.015 g |
| Thyme extract | 0.1 g |
| 1,3 propanediol | 5 g |
| Glycerin | 3 gr |
| Seawater (electrodialyzed to 2.2% NaCl) | q.s. 100.0 g |

Formulation 36

A seawater solution comprising:

| | |
|---|---|
| *Undaria pinnafitida* extract | 0.3 g |
| *Eucalyptus* oil | 0.0075 g |
| Spearmint oil | 0.015 g |
| Thyme extract | 0.1 g |
| 1,3 propanediol | 5 g |
| Glycerin | 3 gr |
| Seawater (electrodialyzed to 2.2% NaCl) | q.s. 100.0 g |

Preparation of Solutions of Formulations 33-36

Following the method of U.S. Pat. No. 6,451,352, these formulations may be prepared by electrodialyzing seawater to the desired osmolarity. Then, a first mix is made by adding algae ingredients and Thyme extract in electodialyzed water. A second mix in a smaller volume of electrodialyzed seawater is created and mixed, glycerin is then added with intense stirring over 30 minutes, then all mixes are pooled to the final volume adjusting the final osmolarity with electrodialyzed seawater of the appropriate osmolarity.

Seawater Used to Prepare Samples

The seawater solution to be used for the preparation of these solutions is preferably derived from dedicated seawater collection sites from a depth of 5-10 meters in zones characterized by the presence of strong currents (which guarantee continuous replenishment of fresh water). The seawater, upon collection, may be typically filtered to remove organic contaminants and/or microorganisms.

A collection site is at the Cancale Bay, Bretagne, France, see EP 0909184. Specifications of the seawater collected at Cancale Bay are presented in Table 4.

TABLE 4

Specifications of Seawater.

| CONTROL | SPECIFICATIONS | METHOD |
|---|---|---|
| Appearance | Colorless clear liquid | Organoleptic |
| Odor | Characteristic | Organoleptic |
| pH (20° C.) | 7.5-8.5 | Eur. Pharm. 7/2.2.3 |
| Density (20° C.) | 0.975-1.078 g/ml | Eur. Pharm. 7/2.2.5 |
| Arsenic | <2 ppm | Eur. Pharm. 7/2.4.2 |
| Heavy metals | <1 ppm | Eur. Pharm. 7/2.4.8 |
| Osmolality | 1000-1200 mOsm/L | Eur. Pharm. 7/2.2.35 |
| TOC | <50 ppm | Eur. Pharm. 7/2.2.44 |
| NaCl Content | 29.0-34.0 g/l | Volhard Method |
| Total hydrocarbon | <1 mg/l | St. Methods/503A |
| Total aerobic microbial Count | <1000 cfu/ml | Eur. Pharm. 7/2.6.12 |
| Yeasts and moulds Count | <100 cfu/ml | Eur. Pharm. 7/2.6.12 |
| Enterobacteria | <10 cfu/ml | Eur. Pharm. 7/2.6.13 |
| *Staphylococcus aureus* | Absence/10 ml | Eur. Pharm. 7/2.6.13 |
| Thermotolerant coliforms | Absence/10 ml | Eur. Pharm. 7/2.6.13 |
| *Pseudomonas aeruginosa* | Absence/10 ml | Eur. Pharm. 7/2.6.13 |

Formulation 37

A saline solution comprising

| | |
|---|---|
| Magnesium Chloride | 2 g |
| Magnesium Bromide | 0.05 g |
| Magnesium sulfate | 0.05 g |
| Potassium Chloride | 1.00 g |
| Calcium Chloride | 0.05 g |
| Sodium Carbonate | 0.05 g |
| *Undaria pinnafitida* extract | 0.3 g |
| 1% saline solution | q.s. 100 g |

Formulation 38

A saline solution comprising

| | |
|---|---|
| Magnesium Chloride | 2 g |
| Magnesium Bromide | 0.05 g |
| Magnesium sulfate | 0.05 g |
| Potassium Chloride | 1.00 g |
| Calcium Chloride | 0.05 g |
| Sodium Carbonate | 0.05 g |
| *Undaria pinnafitida* extract | 0.3 g |
| *Spirulina platensis* extract | 0.5 g |
| 1% saline solution | q.s. 100 g |

Formulation 39

A saline solution comprising

| | |
|---|---|
| Magnesium Chloride | 2 g |
| Magnesium Bromide | 0.05 g |
| Magnesium sulfate | 0.05 g |
| Potassium Chloride | 1.00 g |
| Calcium Chloride | 0.05 g |
| Sodium Carbonate | 0.05 g |
| *Undaria pinnafitida* extract | 0.3 g |
| *Spirulina platensis* extract | 0.5 g |
| Iota-Carrageenan | 0.16 g |
| 1% saline solution | q.s. 100 g |

Formulation 40

A saline solution comprising

| | |
|---|---|
| Sodium Chloride | 3 g |
| *Undaria pinnafitida* extract | 0.3 g |
| *Spirulina platensis* extract | 0.5 g |
| Purified water | q.s. 100 g |

Formulation 41

A saline solution comprising

| | |
|---|---|
| Magnesium Chloride | 2 g |
| Magnesium Bromide | 0.05 g |
| Magnesium sulfate | 0.05 g |
| Potassium Chloride | 1.00 g |
| Calcium Chloride | 0.05 g |
| Sodium Carbonate | 0.05 g |
| *Undaria pinnafitida* extract | 0.3 g |
| Dexpanthenol | 1.0 g |
| 1% saline solution | q.s. 100 g |

Formulation 42

A saline solution comprising

| | |
|---|---|
| Magnesium Chloride | 2 g |
| Magnesium Bromide | 0.05 g |
| Magnesium sulfate | 0.05 g |
| Potassium Chloride | 1.00 g |
| Calcium Chloride | 0.05 g |
| Sodium Carbonate | 0.05 g |
| *Undaria pinnafitida* extract | 0.3 g |
| *Spirulina platensis* extract | 0.5 g |
| Dexpanthenol | 1.0 g |
| 1% saline solution | q.s. 100 g |

Formulation 43

A saline solution comprising

| | |
|---|---|
| Magnesium Chloride | 2 g |
| Magnesium Bromide | 0.05 g |
| Magnesium sulfate | 0.05 g |
| Potassium Chloride | 1.00 g |
| Calcium Chloride | 0.05 g |
| Sodium Carbonate | 0.05 g |
| *Undaria pinnafitida* extract | 0.3 g |
| *Spirulina platensis* extract | 0.5 g |
| Iota-Carrageenan | 0.16 g |
| Dexpanthenol | 1.0 g |
| 1% saline solution | q.s. 100 g |

Formulation 44

A saline solution comprising

| | |
|---|---|
| Sodium Chloride | 3 g |
| *Undaria pinnafitida* extract | 0.3 g |
| *Spirulina platensis* extract | 0.5 g |
| Dexpanthenol | 1.0 g |
| Purified water | q.s. 100 g |

Saline Samples (Formulations 37-44)

The preparation of saline samples is according to U.S. Pat. No. 7,541,052 (mixing of all ingredients under stirring till the solution becomes clear and homogenous).

After preparation of any of the formulations, the solutions may be filtered using appropriate filters (e.g. 0.22 μM), sterilized by standard methodologies (e.g. γ-irradiation) and used in the preparations of devices delivering the solutions.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A pharmaceutical nasal spray composition comprising:
    an ionic aqueous solution; and
    a purified sulfated polysaccharide or a synthetic fucoidan polysaccharide having an average molecular weight of from 4 kDa to 5 MDa and comprising L-fucose and sulfate ester groups,
    wherein:
    i) the ionic aqueous solution comprises filtered or sterilized seawater;
    ii) the sulfated polysaccharide is in a range of about 0.1% to less than 1% weight content of the composition; and
    iii) the sulfated polysaccharide is purified from an extract isolated from brown algae.

2. The composition of claim 1, wherein the brown algae is *Undaria pinnafitida*.

3. The composition of claim 1 further comprising an extract of a blue/green algae.

4. The composition of claim 3, wherein the extract is isolated from *Spirulina platensis*.

5. The composition of claim 1, wherein the seawater comprises undiluted seawater.

6. The composition of claim 1, wherein the seawater further comprises at least one of purified, distilled, deionized, and filtered water.

7. The composition of claim 1, wherein ionic aqueous solution is in a range of about 10 to about 99.9% weight content of the composition.

8. The composition of claim 1, wherein the composition has an osmolarity value ranging from about 250-350 mOsm/L when the ionic aqueous solution is isotonic, greater than about 350 mOsm/L when the ionic aqueous solution is hypertonic and less than about 250 mOsm/L when the ionic aqueous solution is hypotonic.

9. The composition of claim 1 further comprising at least one substance selected from essential oils and plant extracts.

10. The composition of claim 1 further comprising dexpanthenol as hydrating agent.

11. The composition of claim 10, wherein dexpanthenol is present at a concentration ranging from 0.25-2.5% w/w.

12. The composition of claim 1 wherein the purification of the extract isolated from brown algae includes filtration.

13. The composition of claim 12 wherein the filtration allows for collection of molecules of less than about 10 MDa, less than about 5 MDa, less than about 1 MDa, less than about 500 kDa, less than about 300 kDa, less than about 100 kDa or less than about 50 kDa.

14. A pharmaceutical nasal spray composition comprising:
    an ionic aqueous solution; and
    a purified sulfated polysaccharide or a synthetic fucoidan polysaccharide having an average molecular weight of from 4 kDa to 5 MDa and comprising L-fucose and sulfate ester groups, wherein
    i) the ionic aqueous solution comprises at least one of filtered seawater or sterilized seawater;
    ii) the sulphated polysaccharide is in a range of about 0.1% to about 0.3% weight content of the composition; and
    iii) the sulphated polysaccharide is purified from an extract isolated from brown algae.

15. A pharmaceutical nasal spray composition comprising:
    an ionic aqueous solution; and
    a synthetic fucoidan polysaccharide having an average molecular weight of from 4 kDa to 5 MDa and comprising L-fucose and sulfate ester groups, wherein
    i) the ionic aqueous solution comprises at least one of filtered seawater or sterilized seawater; and
    ii) the sulphated polysaccharide is in a range of about 0.1% to about 0.3% weight content of the composition.

* * * * *